US005573005A

United States Patent [19]
Ueda et al.

[11] Patent Number: 5,573,005
[45] Date of Patent: Nov. 12, 1996

[54] EXPIRATION COLLECTING METHOD AND AUTOMATIC EXPIRATION COLLECTOR

[75] Inventors: Hideo Ueda, Osaka; Mitsuo Hiromoto, Kyoto; Meng Gang, Kyoto; Yutaka Yamasaki, Kyoto, all of Japan

[73] Assignee: Kyoto Dai-ichi Kagaku Co. Ltd., Kyoto, Japan

[21] Appl. No.: 327,585

[22] Filed: Oct. 24, 1994

[30] Foreign Application Priority Data

Oct. 25, 1993 [JP] Japan .................................. 5-290132

[51] Int. Cl.$^6$ ........................................... A61B 5/097
[52] U.S. Cl. ........................... 128/730; 128/719; 73/23.3; 422/84
[58] Field of Search ..................... 128/718, 719, 128/730; 422/84; 73/23.3

[56] References Cited

U.S. PATENT DOCUMENTS

| | | | |
|---|---|---|---|
| 3,306,283 | 2/1967 | Arp | 128/719 |
| 3,613,665 | 10/1971 | Gorsuch | 128/730 |
| 4,793,358 | 12/1988 | Kimura | 128/719 |
| 4,818,489 | 4/1989 | Gonner et al. | 128/730 |
| 4,947,861 | 8/1990 | Hamilton | 128/719 |
| 5,042,501 | 8/1991 | Kenny et al. | 128/719 |
| 5,060,656 | 10/1991 | Howard | 128/718 |
| 5,425,374 | 6/1995 | Ueda et al. | 128/719 |

FOREIGN PATENT DOCUMENTS

| | | | |
|---|---|---|---|
| 2541691 | 3/1977 | Germany | 128/719 |
| 9107912 | 6/1991 | WIPO | 128/719 |

*Primary Examiner*—Lee S. Cohen
*Attorney, Agent, or Firm*—Nikaido, Marmelstein, Murray & Oram LLP

[57] ABSTRACT

A syringe for collecting expiration is switched, to be connected by a three-way electromagnetic valve, between an expiration blowing part and a measuring part, so that expiration, blown from the expiration blowing part, is collected in the syringe while replacing old expiration. A switching valve is closed upon completion of exhalation so that end-tidal air is collected in the syringe. Thereafter the expiration sample is introduced into the measuring part from the syringe so that a constant amount of the expiration sample is collected by the measuring part to be introduced into a column.

9 Claims, 4 Drawing Sheets

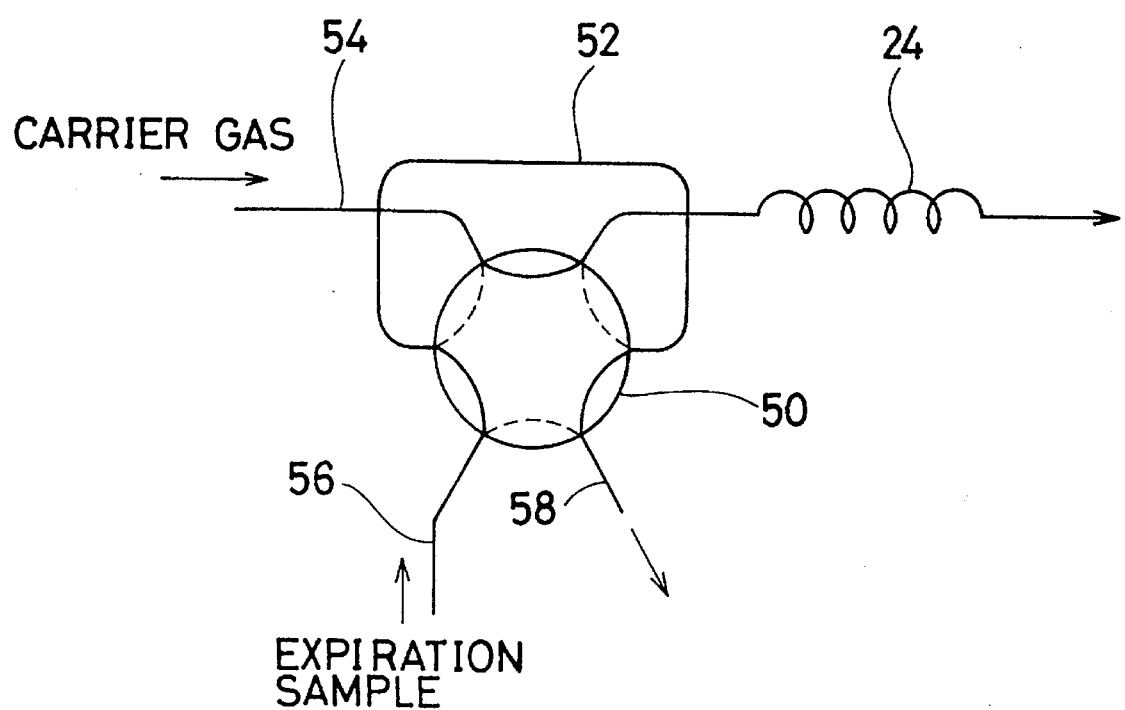

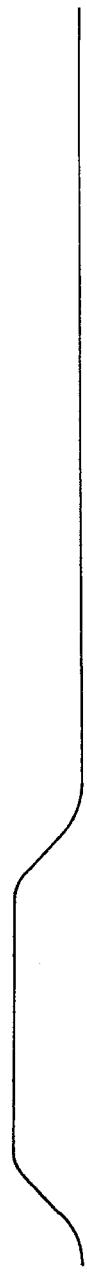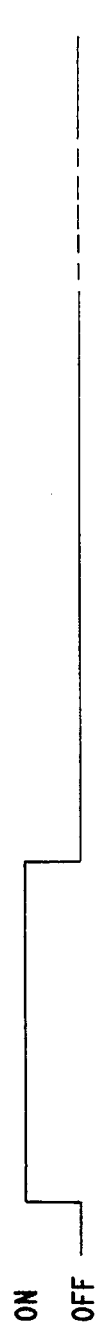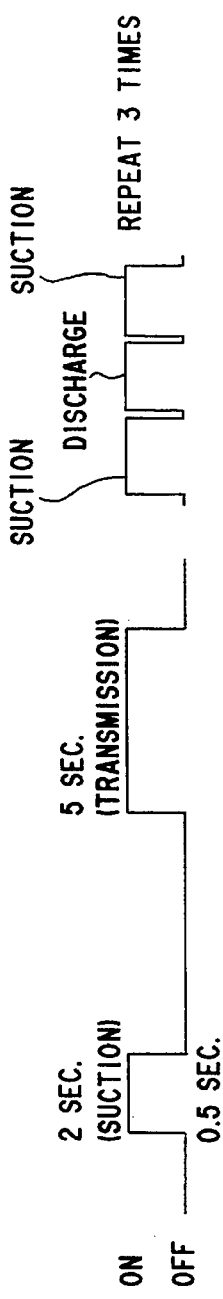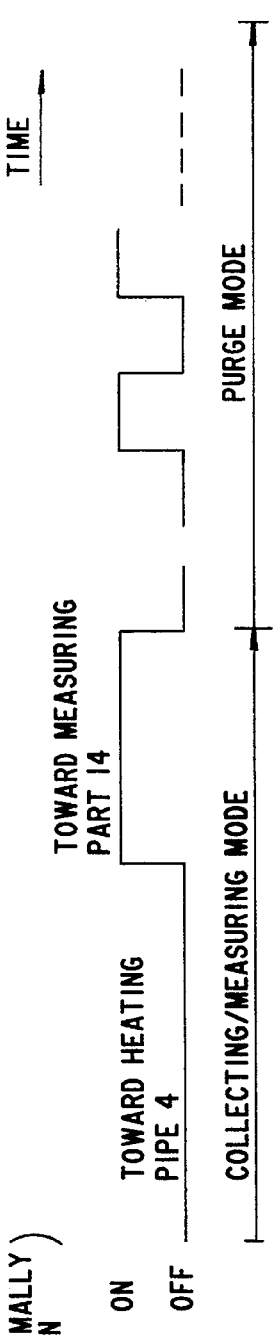

EXPIRATION COLLECTING METHOD AND AUTOMATIC EXPIRATION COLLECTOR

BACKGROUND OF THE INVENTION

1. Field of the Invention

The present invention relates to a method of collecting a constant amount of expiration from a subject for analyzing the expiration collected from the subject as a sample by an analyzer such as a gas chromatograph, a $CO_2$ sensor or the like, and an automatic expiration collector.

2. Description of the Background Art

A clinical test for diagnosing, curing or preventing a disease is generally made on blood or urine. On the other hand, expiration is employed in the laboratory level as a specimen for a clinical biochemical test other than those for blood and urine, leading to such recognition that expiration also includes information as to a disease.

Methods of collecting a specimen of expiration for measuring components of the expiration specimen by an analyzer such as a gas chromatograph are roughly classified into three types, i.e., a chemical trap method of blowing expiration into a solvent for dissolving the former in the latter, a cold trap method of blowing a large amount of expiration into a cold trap which is cooled to about $-80°$ C., for example, for condensing the same, and an adsorption trap method of adsorbing expiration components to an adsorption trap which is charged with activated carbon or adsorption resin (Scientific American, July 1992, pp. 52–57). Among these, the cold trap method and the adsorption trap method have already been put into practice.

In the cold trap method, the sample as trapped is generally partially injected into a gas chromatograph through a micro syringe, to be subjected to analysis. However, it is extremely difficult to put this method into practice as clinical test means for a hospital routine which must be quickly and readily carried out while bringing the analyzer into the bedside of a patient.

In the adsorption trap method, expiration components which are adsorbed by the trap are heated and desorbed to be introduced into a gas chromatograph. However, this method is not suitable for a clinical test for a routine which must be quickly and readily carried out while bringing the analyzer into the bedside of a patient either, in addition to such an essential problem that adsorptivity of the adsorption trap is varied with the components.

A gas measurer such as a gas chromatograph is now being put into practice as a clinical test appliance with improvement of sensitivity, miniaturization and a technique of implementing portability. When such a gas measurer is applied to an expiration analyzer for carrying out a quick clinical test, it is necessary to simply collect expiration in a gas state without trapping the same by a cold trap or an adsorption trap, for directly guiding the expiration to the analyzer so that reliable test data can be obtained in a short time. In order to attain high practicality of such a clinical test appliance, it is necessary to simplify the operation for collecting expiration which is employed as a specimen.

SUMMARY OF THE INVENTION

An object of the present invention is to provide an expiration collecting method which can automatically collect expiration and guide the same to an analyzer through a simple operation while preventing a collection error, and an apparatus for implementing this method.

A first part of expiration exhaled in a single breath contains air from a dead space of an airway portion, which must be eliminated for precise expiration component analysis. The remaining part of the expiration is called end-tidal air, which contains expiration components in homogeneous concentration and is excellent as a specimen. Thus, it is preferable to collect the end-tidal air or expiration from which the air from the dead space is eliminated.

In order to collect the end-tidal air, a first method according to the present invention is adapted to incorporate expiration from a subject in a sample collecting vessel having a volume which is smaller than a single expiration volume (output of single breath) under atmospheric pressure and larger than a volume required for analysis to be capable of replacing precedently blown expiration by subsequently blown one through an expiration inlet and an expiration outlet, and to collect a constant amount of the expiration from the sample collecting vessel upon completion of the single exhalation into the sample collecting vessel for guiding the same to an analyzer. Old expiration contained in the sample collecting vessel is replaced by new expiration while the breath is blown into the sample collecting vessel, whereby the sample collecting vessel stores end-tidal air upon completion of the exhalation. Such completion of the exhalation can be detected by a flow sensor which is provided in a passage for the expiration, for example.

The componential concentration is stabilized in a rear part of expiration, which may not be end-tidal air, and hence a point of time of such stabilization may alternatively be detected with reference to a start time of exhalation, for controlling collection timing. A second method according to the present invention is adapted to control the collection timing in response to the start time of exhalation. The start time of exhalation can also be detected by a flow sensor which is provided in the passage for expiration, for example.

In place of temporarily incorporating the expiration in the sample collecting vessel and collecting a constant amount of the expiration from the sample collecting vessel, a point of time of end-tidal air or a rear part of exhalation may be detected from the passage for the expiration by a flow sensor for collecting a constant amount of the expiration from the passage, or a specific component of the expiration may be detected and monitored so that a constant amount of the expiration is collected from the passage when the component reaches a constant value.

An automatic expiration collector according to the present invention for implementing the first method of collecting end-tidal air comprises an expiration blowing part, a flow sensor which is provided in a passage for expiration blown from the expiration blowing part for detecting the flow of the expiration, a sample collecting vessel having a variable volume, for replacing precedently received expiration by subsequently received expiration through an expiration inlet for receiving the expiration which is supplied from the expiration blowing part and discharging the expiration as collected and a switchable expiration outlet for discharging the received expiration as received, a measuring part which is connected to a passage for the expiration moved from the sample collecting vessel for collecting a constant amount of the expiration and guiding the same to the analyzer, a passage switching part for switching connection to the expiration inlet of the sample collecting vessel between the expiration blowing part and the measuring part, a collection control part for enlarging the volume of the sample collecting vessel to a constant level which is smaller than a single expiration volume under atmospheric pressure and larger than a volume required for analysis after detection of the flow of the expiration made by the flow sensor in a state of connecting the expiration blowing part to the expiration inlet of the sample collecting vessel, closing the expiration outlet of the sample collecting vessel upon detection made by the flow sensor on stopping of the flow of the expiration, and switching the passage switching part for connecting the expiration inlet of the sample collecting vessel to the measuring part thereby moving the expiration which is collected in the sample collecting vessel, and heating means for heating at least the expiration blowing part, the sample collecting vessel, the measuring part and the passage switching part to a temperature exceeding the body temperature of a subject.

The flow sensor detects starting and completion of exhalation. When exhalation is started, the volume of the sample collecting vessel is enlarged on the basis of a signal from the flow sensor. The exhalation still continues so that precedently received expiration is replaced by new expiration in the sample collecting vessel. When the flow sensor detects completion of the exhalation, the expiration outlet is closed so that the sample collecting vessel collects end-tidal air. The expiration collected in the sample collecting vessel is thereafter transmitted to the measuring part by a collection driving mechanism or a suction mechanism, so that a constant amount thereof is collected in the measuring part to be guided to the analyzer for analysis.

The expiration contains moisture, which is disadvantageously condensed in the expiration passage if the passage is at a temperature lower than the body temperature of the subject such as a human or an animal, and water-soluble components contained in the expiration are dissolved in the condensed moisture to make difficulty in correct quantitative analysis of the expiration components. Therefore, the heating means heats portions which come into contact with the expiration to be guided to the analyzer to a temperature exceeding the body temperature of the subject, e.g., to 40° to 50° C. on the inner wall of the expiration passage, for example, thereby preventing loss of the expiration components caused by condensation of the moisture which is contained in the expiration.

The analyzer can be formed by a gas chromatograph or a measurer comprising a $CO_2$ sensor (NDIR (nondispersive infrared analyzer)), an electrochemical $0_2$ sensor, a CO sensor or a combustible gas sensor (semiconductor sensor), but is not restricted to these.

A gas chromatograph which is employed as the analyzer must be of high sensitivity, miniaturized and capable of being in a portable structure, in consideration of application to a clinical test. The gas chromatograph is formed by a carrier gas supply part, a separation column and a detector. The separation column may be prepared from either a capillary column or a packed column, which is properly selected in response to the target gas. The detector is preferably prepared from that of high sensitivity which is suitable for miniaturization, such as a PID (photoionization detector), an IMS (ionic mobility spectrum detector) or an ECD (electron capture detector), which is adapted to apply light or radiation to target gas components contained in expiration for ionizing the same and outputting a measuring signal in response to the amount of ionization. Such a detector is safe as compared with an FID (flame ionization detector) or an FPD (flame photometric detector) accompanied by combustion of hydrogen gas, can be miniaturized, and is capable of carrying out detection in high sensitivity and high accuracy. Further, low-priced air or gaseous nitrogen can advantageously be employed as the carrier gas.

The measuring part is adapted to first feed expiration which is delivered from the sample collecting vessel through a measuring tube or a measuring chamber of a constant volume and to switch to connect the measuring tube or the measuring chamber to a passage communicating with the analyzer in collection, thereby introducing the expiration sample collected in the measuring tube or the measuring chamber to the analyzer by the carrier gas. Such a measuring part can be formed by means of any arbitrary structure such as that generally employed as sample collecting means in a gas chromatograph.

A volume of exhalation in a single breath of a human is generally 0.5 to 2.5 liters under the atmospheric pressure. Thus, it is preferable to set the enlarged volume of the sample collecting vessel at about 50 to 250 ml, i.e., about $\frac{1}{10}$ of the volume of exhalation so that precedently collected expiration is sufficiently replaced by subsequently collected expiration in the sample collecting vessel, while setting the volume of the measuring part at about 20 to 1000 μl, for example.

According to the present invention, expiration is collected from the subject in the sample collecting vessel having a volume which is smaller than a single exhalation volume under atmospheric pressure and larger than a volume required for analysis and being capable of replacing precedently blown expiration by subsequently blown expiration through the expiration inlet and the expiration outlet so that a constant amount of the expiration is collected from the sample collecting vessel upon completion of single exhalation into the sample collecting vessel or a rear part of the expiration, whereby proper sample collection can be carried out regardless of difference in exhalation and timing among subjects. Further, it is not necessary to adjust sample collection timing in response to the vital capacity of the subject, leading to substantially no failure of sample collection. The expiration specimen which is collected in this manner is formed by end-tidal air or a part close thereto regardless of the vital capacity of the subject, whereby componential concentration is stabilized and quantitative accuracy is improved.

Further, the present invention is adapted to automatically carry out expiration collection, whereby the subject can only breathe out through the expiration blowing part so that the collector thereafter automatically collects the expiration for guiding the same to the analyzer. Thus, a doctor or a nurse who is inexperienced in operation of the appliance can readily collect and analyze the expiration of the patient.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a passage diagram showing an exemplary measuring part provided in the embodiment;

FIG. 3 is a diagram showing the operation of the embodiment; and

DESCRIPTION OF THE PREFERRED EMBODIMENTS

Figure 1:
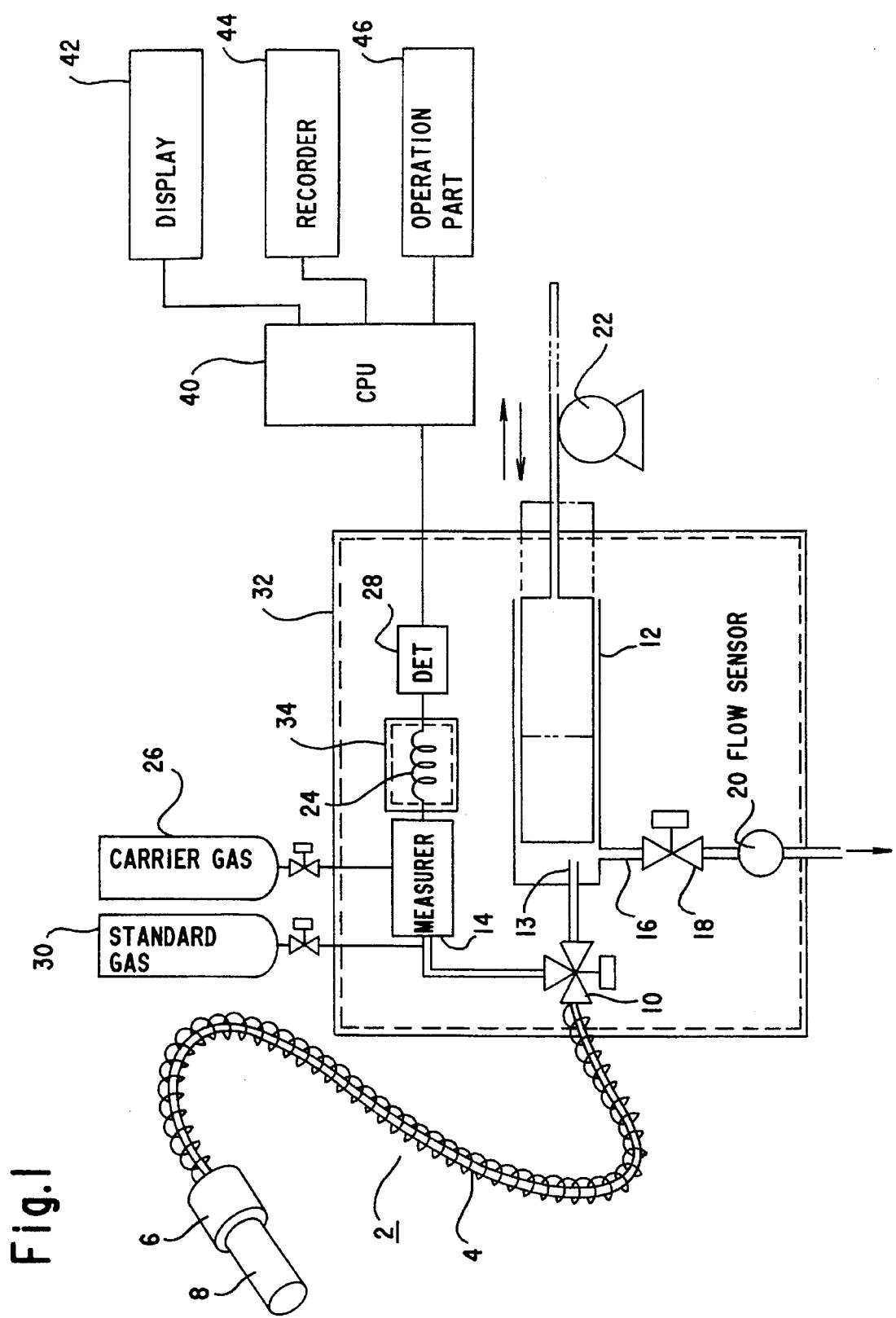
FIG. 1 is a schematic block diagram showing an embodiment of the present invention.

FIG. 1 shows an embodiment of the present invention. However, the present invention is not restricted to this embodiment.

An expiration blowing part 2 comprises a mouthpiece 8 for exhalation, which is detachably mounted on a heating pipe 4 through a mouthpiece holder 6. The heating pipe 4 is formed by winding a heater on a tube, which is preferably made of an elastic material such as polytetrafluoroethylene, for example, so that the same will neither adsorb nor react with gas contained in the expiration and is easy to handle. The heater is temperature-controlled to heat the inner wall of the tube to 40° to 50° C., so that moisture contained in the expiration is not condensed on the inner wall. The mouthpiece 8 can be formed by a commercial item, which is employed for a vital capacity test, for example. This mouthpiece 8 is preferably formed by a disposable one, in consideration of sanitation and management. The mouthpiece 8 may be prepared from a natural or synthetic material, which must generate neither gas nor smell.

A base portion of the heating pipe 4 is connected to one connection port of a three-way electromagnetic valve 10. Remaining connection ports of the three-way electromagnetic valve 10 are connected to a syringe 12 serving as a sample collecting vessel and a measuring part 14 respectively. The three-way electromagnetic valve 10 is adapted to switch connection to the syringe 12 between the heating pipe 4 and the measuring part 14. The three-way electromagnetic valve 10 connects the syringe 12 to the heating pipe 4 for attaining communication therebetween in order to collect expiration in the syringe 12, while the same switches the passage so that the syringe 12 communicates with the measuring part 14 in order to introduce the expiration collected in the syringe 12 into the measuring part 14.

The syringe 12 is provided in its frontmost end beyond a piston with a space, which is provided with an expiration inlet 13 communicating with the three-way electromagnetic valve 10 and an expiration outlet 16 communicating with an exhaust port to the exterior. A switching valve 18 is provided in a passage communicating with the expiration outlet 16, while a flow sensor 20 for detecting a gas flow is provided downstream of the switching valve 18. The switching valve 18 is opened in exhalation, so that the flow sensor 20 detects the expiration flow when the expiration received through the three-way electromagnetic valve 10 is discharged from the expiration outlet 16 through the flow sensor 20. The switching valve 18 is closed when stopping of the expiration flow is detected, so that end-tidal air is collected in the syringe 12.

The content volume of the syringe 12 is changed when its piston rod is moved by a syringe driving mechanism including a motor 22. The motor 22 operates under control by a CPU 40, to retract the piston to a position shown by chain lines for enlarging the content volume of the syringe 12 to 50 ml, for example, and stop the piston when the flow sensor 20 detects the expiration flow, while pushing the piston to discharge the expiration collected in the syringe 12 when the flow sensor 20 detects stopping of the expiration flow.

A column 24 of a gas chromatograph serving as an analyzer is connected downstream the measuring part 14, so that carrier gas received from a carrier gas cylinder 26 flows into the column 24 through the measuring part 14. In sample collection, an expiration sample which is collected by the measuring part 14 is introduced into the column 24 with the carrier gas from the carrier gas cylinder 26. A PID serving as a detector 28 is arranged downstream of the column 24.

A standard gas cylinder 30 is connected to a passage upstream the measuring part 14 for forming a calibration curve which is employed for determination of the expiration components, so that standard gas is collected by the measuring part 14 and introduced into the column 24.

The three-way electromagnetic valve 10, the syringe 12, the switching valve 18, the flow sensor 20, the measuring part 14, the column 24 and the detector 28 are stored in a thermostat 32 which is controlled at a constant temperature of 50° C., for preventing condensation of moisture contained in the expiration as collected during introduction into the column 24 while maintaining the column 24 and the detector 28 at constant temperatures. The column 24 is further stored in a column oven 34 which is provided in the thermostat 32, to be further prevented from temperature fluctuation.

The CPU 40 is provided as a data processing/control unit for automatically driving this expiration collector, serving as a collection control part of receiving an input signal from an operation part 46 and inputting a detection signal from the flow sensor 20 for controlling operations of the three-way electromagnetic valve 10, the switching valve 18 and the motor 22, and controlling the sample collecting operation of the measuring part 14, and for incorporating a detection signal from the detector 28 for identifying the expiration components and calculating concentration values of the expiration components from previously measured and stored calibration curve data, and manages the operation program for the overall expiration collector. A display part 42 such as a CRT is provided for displaying analytical results of the expiration as measured, while a recorder 44 is provided for recording the analytical results.

FIG. 2 shows an example of the measuring part 14.

The exemplary measuring part shown in FIG. 2 employs a hexagonal cock 50, which is generally used as a gas sample introducer for a gas chromatograph. A measuring tube 52 is connected to the hexagonal cock 50 and a carrier gas passage 54 from the carrier gas cylinder 26 is connected to be switched between the measuring tube 52 and the column 24 by the hexagonal cock 50, while a sample passage 56 receiving the expiration from the syringe 12 through the three-way electromagnetic valve 10 is connected to be switched between the measuring tube 52 and a discharge port 58 by the hexagonal cock 50.

In order to collect an expiration sample by this measuring part, the hexagonal cock 50 is switched from passages shown by solid lines to those shown by broken lines while the expiration sample is discharged through the measuring tube 52. Thus, the sample which is collected by the measuring tube 52 is introduced into the column 24 with the carrier gas.

The structure of the measuring part 14 is not restricted to that shown in FIG. 2, but this part 14 can be formed by any sample introducer which is employed for introducing a gas sample into an analyzer in a gas chromatograph or the like.

The operation of this embodiment is now described with reference to FIG. 3.

At first, the syringe 12 is in a pushed state, the switching valve 18 is opened and the three-way electromagnetic valve 10 is set to connect the heating pipe 2 to the syringe 12. When a subject breathes out through the mouthpiece 8, the flow sensor 20 detects the expiration flow. The CPU 40 drives the motor 22 upon a lapse of 0.5 sec. after receiving a detection signal for the expiration flow from the flow sensor 20, to retract the forward end of the piston to the position of the chain lines in 2 seconds, to enlarge the content volume of the syringe 12 to 50 ml. Exhalation is still continued so that precedently received expiration is replaced by subsequently received one in the syringe 12, which in turn collects the new expiration. After completion of the exhalation, the CPU 40 receives a detection output for the stopping of the expiration flow from the flow sensor 20, to close the switching valve 18 and switch the three-way electromagnetic valve 10 thereby connecting the syringe 12 to the measuring part 14. At this time, the syringe 12 collects end-tidal air.

Thereafter the CPU 40 drives the motor 22 to push the piston of the syringe 12, thereby discharging the expiration collected in the syringe 12 into the measuring part 14 in 5 seconds. During such transmission of the expiration from the syringe 12 to the measuring part 14, the CPU 40 switches the hexagonal cock 50 in the measuring part 14 for collecting the expiration sample and transmitting the same to the column 24. The above operation is carried out in a collecting/measuring mode. Thereafter the expiration components are separated from each other in the column 24, detected by the detector 28 and data-processed in the CPU 40.

After the expiration is completely discharged from the syringe 12, the switching valve 18 is opened by a command from the CPU 40, and the three-way electromagnetic valve 10 is switched toward the heating pipe 4. Thereafter the switching valve 18 is closed, the syringe 12 sucks air from the heating pipe 4, and then the three- way electromagnetic valve 10 is switched toward the measuring part 14 to discharge the air from the syringe 12. The operation of sucking air from the heating pipe 4 and discharging the same toward the measuring part 14 is repeated three times, to purge components adhering to the passage. This operation is performed in a purge mode. A single measuring operation is completed through the collecting/measuring mode and the purge mode.

When the mode of purging the components from the expiration passage is provided following the collecting/measuring mode, it is possible to reduce contamination between subjects thereby performing quantitative analysis in higher accuracy.

Figure 4:
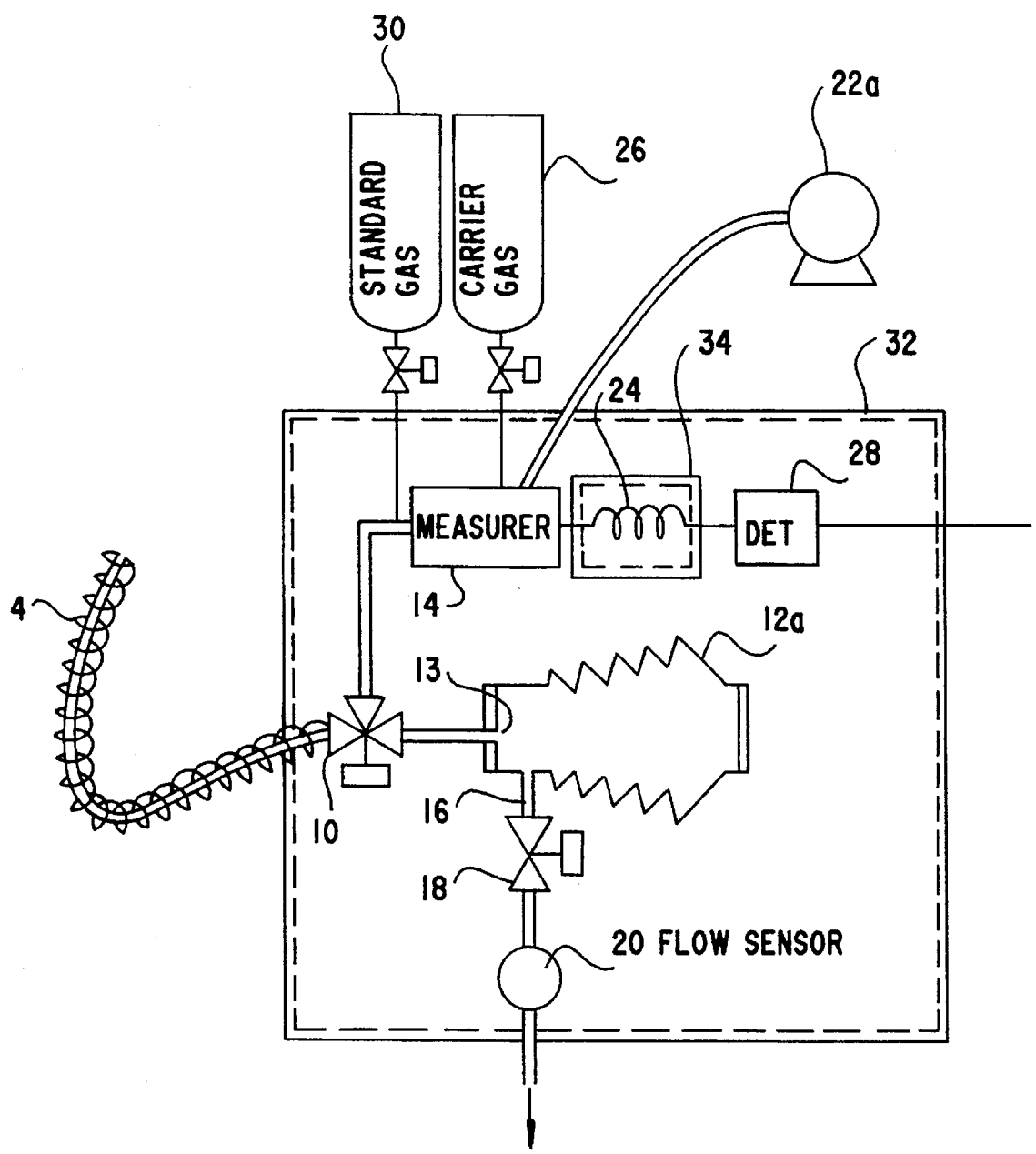
FIG. 4 is a schematic block diagram showing another embodiment of the present invention.

FIG. 4 shows another embodiment of the present invention. In this embodiment, a restorable flexible bag 12a having a variable volume is provided as a sample collecting vessel. This bag 12a can be formed by a TEDLAR bag (trade mark of Du-Pont) having a capacity of 50 to 100 ml, for example. The TEDLAR bag 12a is made of a material causing no loss of measured components such as adsorption and decomposition of a gas component which is contained in expiration. The bag 12a, whose volume can be expanded through its restoring force, comprises no driving source to be contracted by itself. The volume of the bag 12a is reduced when a switching valve 18 is closed to suck air from its interior. An air pump 22a is connected to a discharge port 58 (see FIG. 2) of a measuring/collecting part 14 for introducing expiration which is temporarily stored in the bag 12a into a measuring tube or a measuring chamber of the measuring part 14 and for purging components from a passage for the expiration sample. The air pump 22a is preferably formed by that of a diaphragm type, for example, with a suction volume of about 500 ml/min., to be capable of discharging the expiration sample which is collected in the bag 12a in about 6 to 10 sec.

The embodiment shown in FIG. 4 is basically identical in operation to that shown in FIG. 1, while the pump 22a carries out an operation of transmitting the expiration sample collected in the bag 12a, which is provided in place of the syringe 12, to the measuring part 14 as well as a purge operation. No driving source is required for collecting the expiration sample in the bag 12a. In order to transmit the expiration sample from the bag 12a to the measuring part 14, the pump 22a performs a sucking operation in place of the pushing operation by the motor 22 shown in FIG. 1.

The purge operation is carried out when the sample components are separated in a column 24. A three-way electromagnetic valve 10 is switched toward the bag 12a, so that the bag 12a sucks air from a heating pipe 4 through its restoring force. Then, the three-way electromagnetic valve 10 is switched toward the measuring part 14 and the pump 22a is driven to introduce the air from the bag 12a to the measuring part 14a through an expiration passage, thereby discharging the same through the pump 22a. The operation of sucking air in the bag 12a and discharging the air to the measuring part 14a is repeated three times.

In the embodiment shown in FIG. 4, the flexible bag 12a may alternatively be replaced by a bellows type bag.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An expiration collecting method, comprising the steps of:

receiving expiration from a subject into a sample collecting vessel having a volume smaller than a single expiration volume under atmospheric pressure and larger than a volume required for analysis and replacing precedently blown expiration in said sample collecting vessel by subsequently blown expiration through an expiration inlet and an expiration outlet; and collecting a constant amount of end-tidal air of said expiration from said sample collecting vessel upon completion of a single exhalation into said sample collecting vessel and guiding said constant amount of end-tidal air of said expiration to an analyzer.

2. An expiration collecting method, according to claim 1, wherein after the expiration is guided to said analyzer, further comprising the steps of:

a) sucking air from an expiration blowing part into said sample collecting vessel;

b) discharging said sucked air from said sample collecting vessel; and c) repeating said steps a) and b) two more times to complete a purge node.

3. An expiration collecting method, comprising the steps of:

receiving expiration from a subject into a sample collecting vessel having a volume smaller than a single expiration volume under atmospheric pressure and larger than a volume required for analysis and replacing precedently blown expiration in said sample collecting vessel by subsequently blown expiration through an expiration inlet and an expiration outlet; and collecting a constant amount of said expiration from said sample collecting vessel after a lapse of a constant period from starting of said expiration from said subject, said constant period belonging to a rear half of a single exhalation into said sample collecting vessel, and guiding said constant amount to an analyzer.

4. An expiration collecting method according to claim 3, wherein after the expiration is guided to said analyzer, further comprising the steps of:

a) sucking air from an expiration blowing part into said sample collecting vessel;

b) discharging said sucked air from said sample collecting vessel; and c) repeating said steps a) and b) two more times to complete a purge node.

5. An automatic expiration collector comprising:

an expiration blowing part;

a flow sensor being provided in a passage for expiration being blown from said expiration blowing part, said flow sensor for detecting flow of said expiration;

a sample collecting vessel having a variable volume, said sample collecting vessel for replacing precedently received expiration by subsequently received expiration through an expiration inlet, said expiration inlet receiving said expiration being supplied from said expiration blowing part and discharging collected end-tidal air of said expiration and said sample collecting vessel having a switchable expiration outlet for discharging received said expiration, said switchable expiration outlet connected to said flow sensor;

a measuring part being connected to a passage for said end-tidal air of said expiration moved from said sample collecting vessel, said measuring part for collecting a constant amount of said end-tidal air of said expiration and for guiding the end-tidal air of the expiration to an analyzer;

a passage switching part switchably connecting said expiration blowing part, said sample collecting vessel and said measuring part, said passage switching part for switching connection of said expiration inlet of said sample collecting vessel between said expiration blowing part and said measuring part;

a collection control part, associated with said flow sensor, said sample collecting vessel and passage switching part, said collection control part for enlarging said volume of said sample collecting vessel to a constant level smaller than a single expiration volume under atmospheric pressure and larger than a volume required for analysis after detection of said flow of said expiration made by said flow sensor in a state of connecting said expiration blowing part to said expiration inlet of said sample collecting vessel, for closing said expiration outlet of said sample collecting vessel upon detection made by said flow sensor on stopping of said flow of said expiration, for switching said passage switching part for connecting said expiration inlet of said sample collecting vessel to said measuring part, and thereafter moving said end-tidal air of said expiration collected in said sample collecting vessel to said measuring part; and heating means for heating at least said expiration blowing part, said sample collecting vessel, said measuring part and said passage switching part to a temperature exceeding a body temperature of a subject.

6. An automatic expiration collector in accordance with claim 5, wherein said sample collecting vessel is a syringe having said expiration inlet and said expiration outlet in its forward end portion and comprising a driving mechanism for varying the volume of said syringe, said collection control part being adapted to vary said volume of said syringe between a) a state being provided with a small space in said forward end portion of said syringe for allowing flow of said expiration being received from said expiration inlet of said syringe toward said expiration outlet and b) a state of enlarging said constant volume through said driving mechanism.

7. An automatic expiration collector in accordance with claim 5, wherein said sample collecting vessel is a bag having restoring force being provided with a constant capacity, whose volume is enlarged by supply of said expiration, and comprising a suction mechanism for sucking said expiration being collected in said bag through said measuring part, said collection control part being adapted to suck said expiration sample from said bag by said suction mechanism thereby moving said expiration sample to said measuring part while reducing said volume of said bag.

8. An automatic expiration collector in accordance with claim 7, wherein said bag is a flexible bag.

9. An automatic expiration collector in accordance with claim 7, wherein said bag is a bellows type bag.

* * * * *